United States Patent [19]

Bodis-Wollner

[11] Patent Number: 5,176,147
[45] Date of Patent: Jan. 5, 1993

[54] METHOD AND APPARATUS FOR DETECTING OPTIC NEUROPATHY

[76] Inventor: Ivan G. Bodis-Wollner, 1235 Park Avenue, New York, N.Y. 10128

[21] Appl. No.: 692,891

[22] Filed: Apr. 29, 1990

[51] Int. Cl.⁵ ............................................. A61B 13/00
[52] U.S. Cl. ................................... 128/745; 351/239
[58] Field of Search ................ 128/745; 351/211, 224, 351/237, 239

[56] References Cited

U.S. PATENT DOCUMENTS

| | | | |
|---|---|---|---|
| 4,146,311 | 3/1979 | Murr | 128/745 |
| 4,365,873 | 12/1982 | Ginsburg | 351/239 |
| 4,368,959 | 1/1983 | D'Amato | 128/745 |
| 4,384,768 | 5/1983 | Guzman | 351/237 |
| 4,493,539 | 1/1985 | Cannon | 128/745 |
| 4,526,452 | 7/1985 | Hirsch | 351/239 |
| 4,615,594 | 10/1986 | Task | 351/239 |

OTHER PUBLICATIONS

Caelli et al., On the Detection of Gabor Signals and Discrimination of Gabor Textures, Vision Res. (1985) vol. 25, No. 5, pp. 671-684.

Fogel et al., Gabor Filters as Texture Discriminator, Biol. Cybern. (1989) 61, pp. 103-113.

Wolkstein et al. Contrast Sensitivity in Retinal Disease, Ophthalmology, (1980) vol. 97, No. 11, pp. 1140-1149.

*Primary Examiner*—Max Hindenburg
*Attorney, Agent, or Firm*—Brumbaugh, Graves, Donohue & Raymond

[57] ABSTRACT

A patient is presented with a series of sinusoidal gratings truncated at varying diameters in each quadrant of the visual field (superior nasal, inferior nasal, superior temporal, inferior temporal). The patient fixates on a central point and identifies the point in the series at which he can see the patterns. Comparison of the diameter at which the patient can first perceive the pattern with a standard value provides an indication of not only the existence of optic neuropathy but also the magnitude of the damage.

16 Claims, 6 Drawing Sheets

METHOD AND APPARATUS FOR DETECTING OPTIC NEUROPATHY

BACKGROUND OF THE INVENTION

This application relates to a method and apparatus for the detection of optic neuropathy, particularly detection of glaucoma, brain tumors affecting the optic nervous system and other optic nerve diseases. The method and apparatus exploit the differential ability of normal and optic neuropathy patients to detect paracentrally presented sinusoidal grating patterns truncated at different diameters by a Gaussian aperture.

Sinusoidal grating patterns have been used as part of various test methods for testing foveal vision. The grating pattern appears as a series of bars, the spacing of which depends on the frequency of the sine wave employed to generate the pattern. A generally circular outline is established by truncating the pattern with a Gaussian aperture.

Foveal vision tests are in many cases inadequate for detecting the early signs of glaucoma, brain tumors and other optic nerve diseases. For example, in the early stages of glaucoma, the damage to the optic nerve is diffuse, or may occur in only certain types of neurons rather than being concentrated in individual bundles of the optic nerve. Because of this, discrete field defects may not be detected.

To provide for early detection of the optic nerve damage, therefore, it would be highly desirable to have a mechanism which was capable of detecting diffuse damage to the optic nerve. It is an object of the present invention to fulfill this need.

SUMMARY OF THE INVENTION

It has now been found that sinusoidal grating patterns can be employed paracentrally (parafoveally) to detect optic neuropathy in a patient. In accordance with the invention, the patient is presented with a series of sinusoidal gratings truncated at varying diameters in each quadrant of the visual field (superior nasal, inferior nasal, superior temporal, inferior temporal). The patient fixates on a central point and identifies the point in the series at which he can see the patterns. Comparison of the diameter at which the patient can first perceive the pattern with a standard value provides an indication of not only the existence of optic neuropathy but also the magnitude of the damage.

The invention is advantageously practiced with the aid of an optical display system which is adapted to present a series of diagnostic images to the patient. Each diagnostic image advantageously consists of a centrally located fixation point and four or more truncated sinusoidal grating patterns symmetrically disposed about the fixation point. The optical display system may take the form of a plurality of cards, each having a diagnostic image disposed thereon, or may be in the form of transparencies, video tape or other display means capable of producing a consistent image.

DETAILED DESCRIPTION OF THE INVENTION

Figure 1:
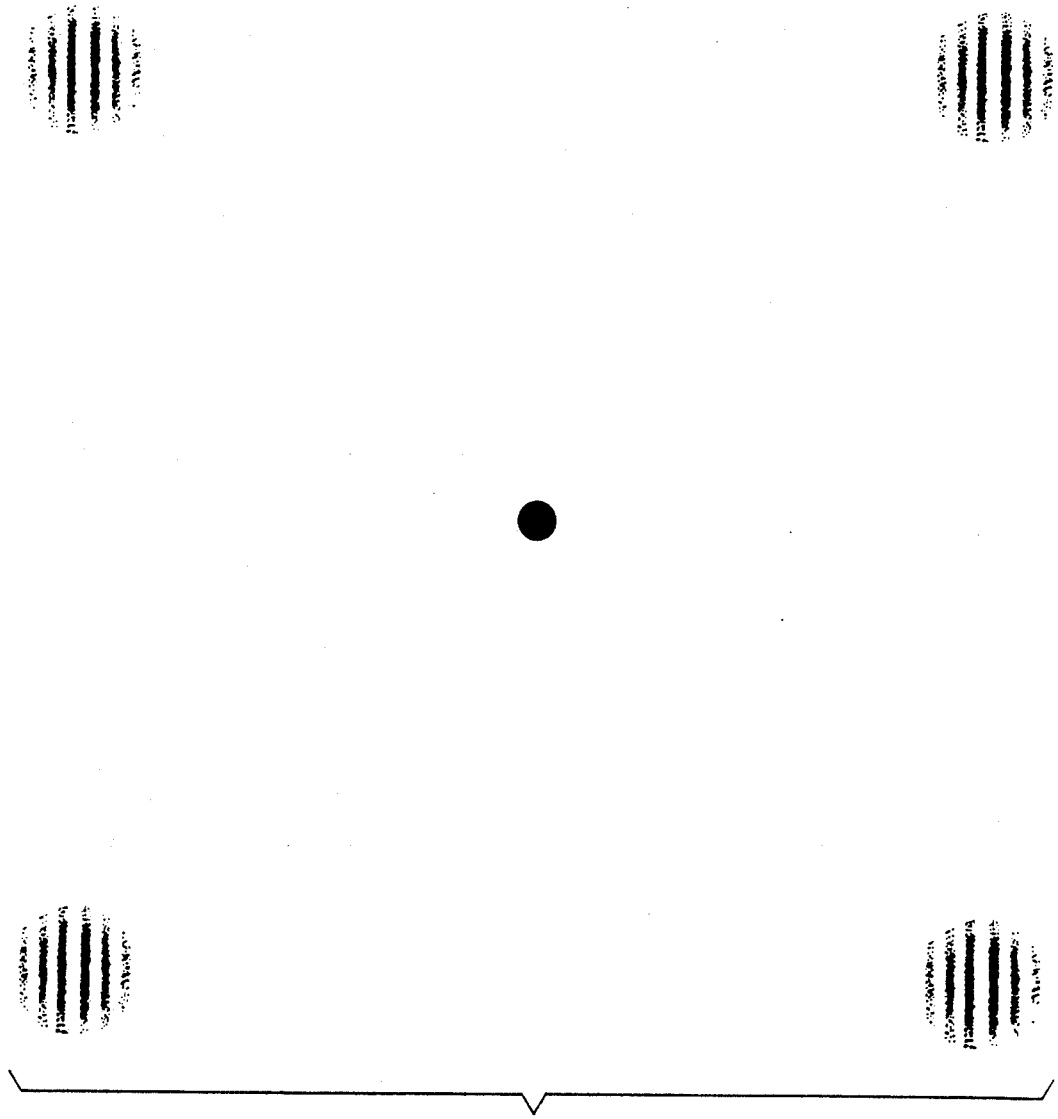
FIGS. 1 and 2 show diagnostic images in accordance with the invention.

Grating patterns may be defined in terms of the spatial frequency, i.e., the number of dark and bright bands subtending 1 degree of Visual angle at the observers eye; and the spatial contrast C which is given by the equation $$C = \frac{L_{max} - L_{min}}{L_{max} + L_{min}}$$

wherein $L_{max}$ and $L_{min}$ are the maximum and minimum luminance. In addition, the diameter of the grating pattern can be described in terms of the diameter of a Gaussian aperture which is used to truncate the grating pattern.

Gratings useful in the present invention are those which have spatial frequencies of 0.5 to 6, preferably 1 to 4 cycles/deg; contrasts of 1% to 90%, preferably 2% to 60%; and diameters of from 1 to 16 degrees of visual angle, preferably 1 to 8 degrees. It will be understood that the spatial frequency and diameter of the spot do not fall within a specific absolute range since they depend on the intended distance between the eye of the patient and the grating being observed. Exemplary specific numbers, however, are indicative of the types of values considered appropriate. For example, if the patient is 30 cm from the diagnostic image, a pattern with a diameter of from 0.5 to 4 cm will span the range from 1 to 8 degrees of visual angle, and these spots may include from 1 to 48 bars. As will be recognized by the person skilled in the art, the grating patterns used in the invention thus coincide to what are commonly referred to as "Gabor patches."

The grating patterns may be formed of black and white bands, or they may be colored (for example red and green or blue and yellow). The results observed with black and white versus color patterns may be different, for example, if a patient has lost luminance processing as opposed to color processing ability.

To be used in the present invention, the grating pattern is presented to the patient in each quadrant of the visual field, with the peak contrast of the pattern being located from 2 to 40 degrees, preferably 4 degrees of visual angle from the fixation point. To determine whether there is optic neuropathy, the patient, with one eye blocked, may be shown a single series of grating patterns, all with the same contrast, and asked to identify what he sees in each quadrant.

Control or "catch" cards with only three quadrants filled in or with the pattern in one quadrant different in contrast from the remaining patterns may be included in the series without departing from the scope of the invention. It has been found that the ability to perceive the grating pattern has a basically sigmoidal relationship to the size of the aperture. For spatnional frequency of 1 cycle/degree, this sigmoidal curve is centered (semi-saturation constant) at a diameter corresponding to an aperture size of about 4.5 degrees for normal individuals. For individuals with diagnosed glaucoma, the value is higher, about 7.7 degrees on average. In normal individuals, the standard deviation on the measurements appears to be about 0.6 degrees and this figure provides an appropriate measure of the difference in aperture between adjacent members of the series. These standard values can be used to check an individual for signs of optic neuropathy by presenting a series of grating patterns, having a constant contrast and spatial frequency but varying diameter.

Figure 2:
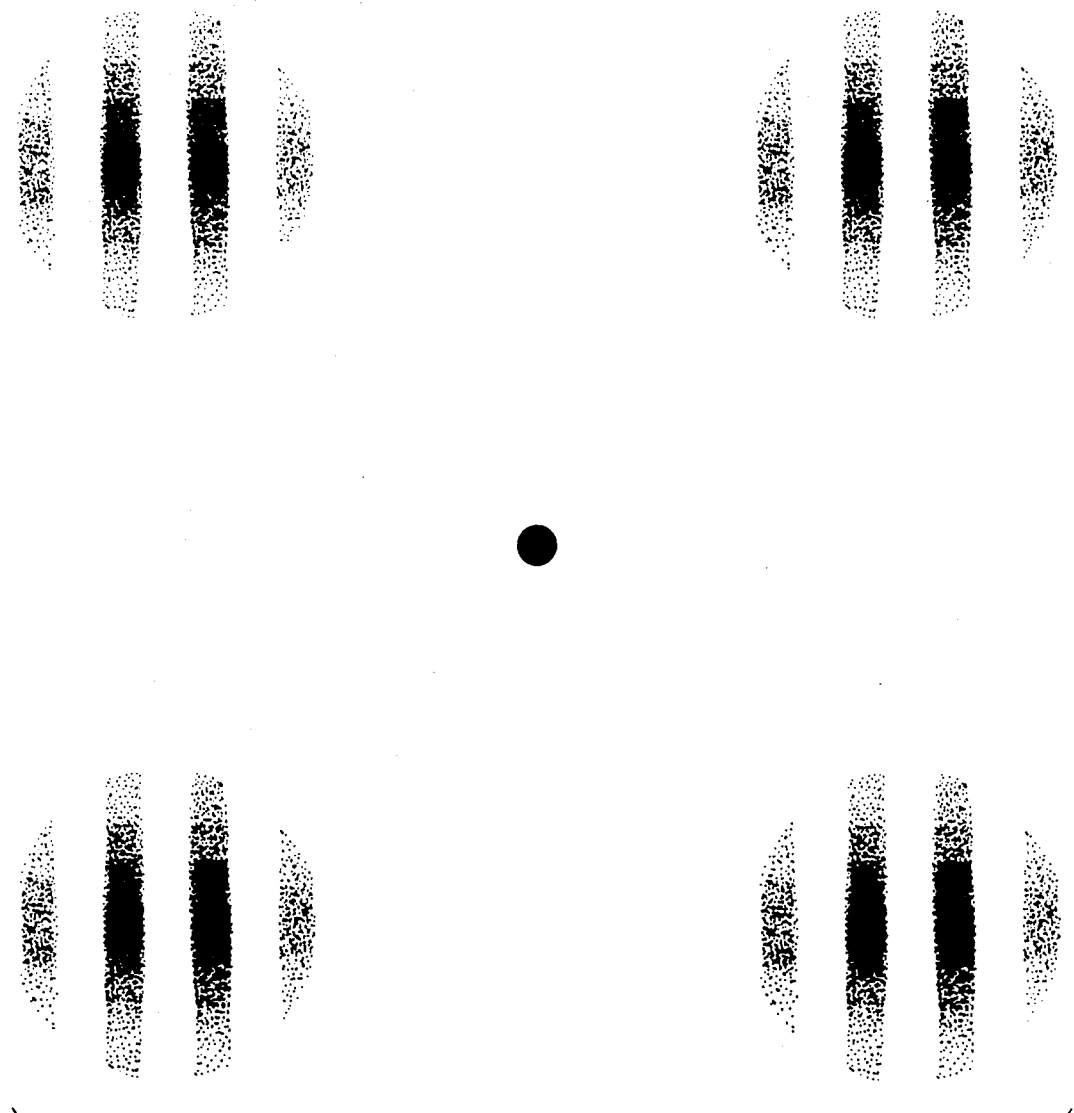

In a preferred test format, each member of the series is a diagnostic image comprising a central fixation point and at least four grating pattern disposed symmetrically about the fixation point. (FIGS. 1 and 2) The patient is asked to view the diagnostic image and state whether he can see the patterns. By comparing the diameter of the smallest grating where the pattern can be perceived with the established standard for that set of gratings, the existence of optic neuropathy can be assessed.

Figure 3:
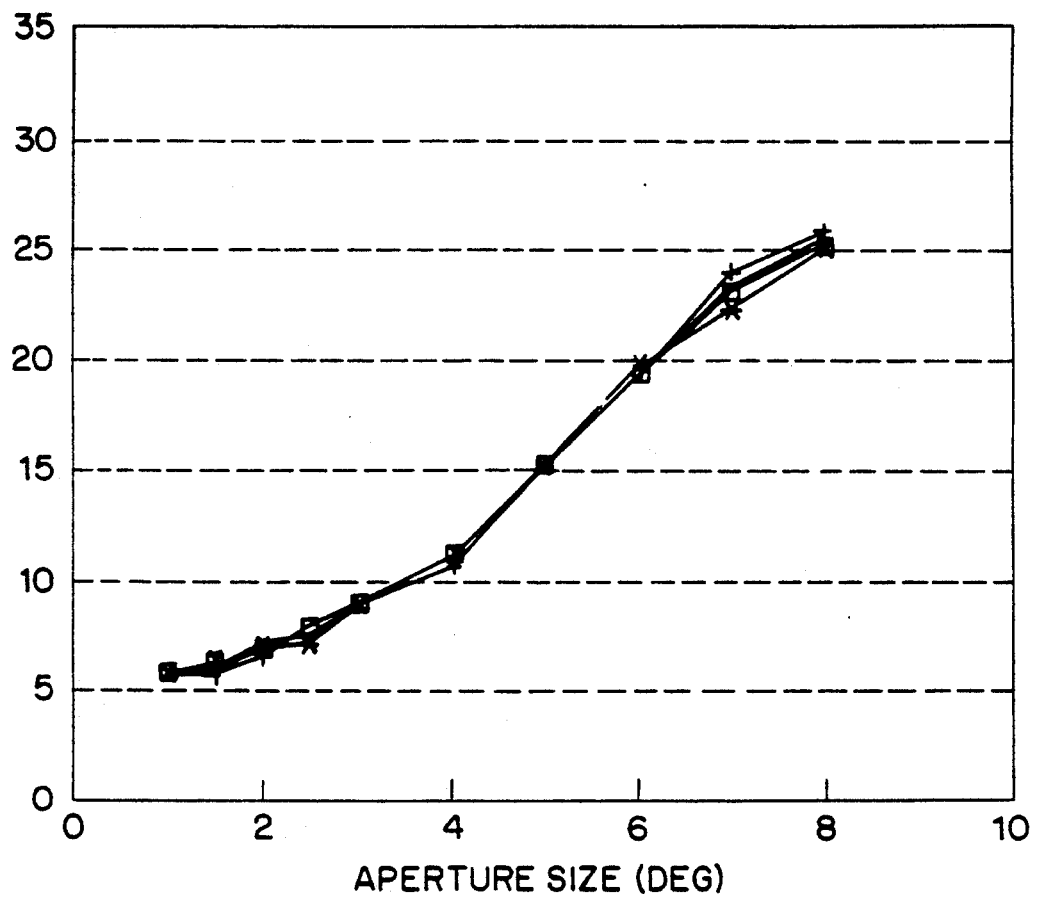
FIG. 3 shows a graph of contrast sensitivity as a function of aperture size for 7 normal individuals.
Figure 4:
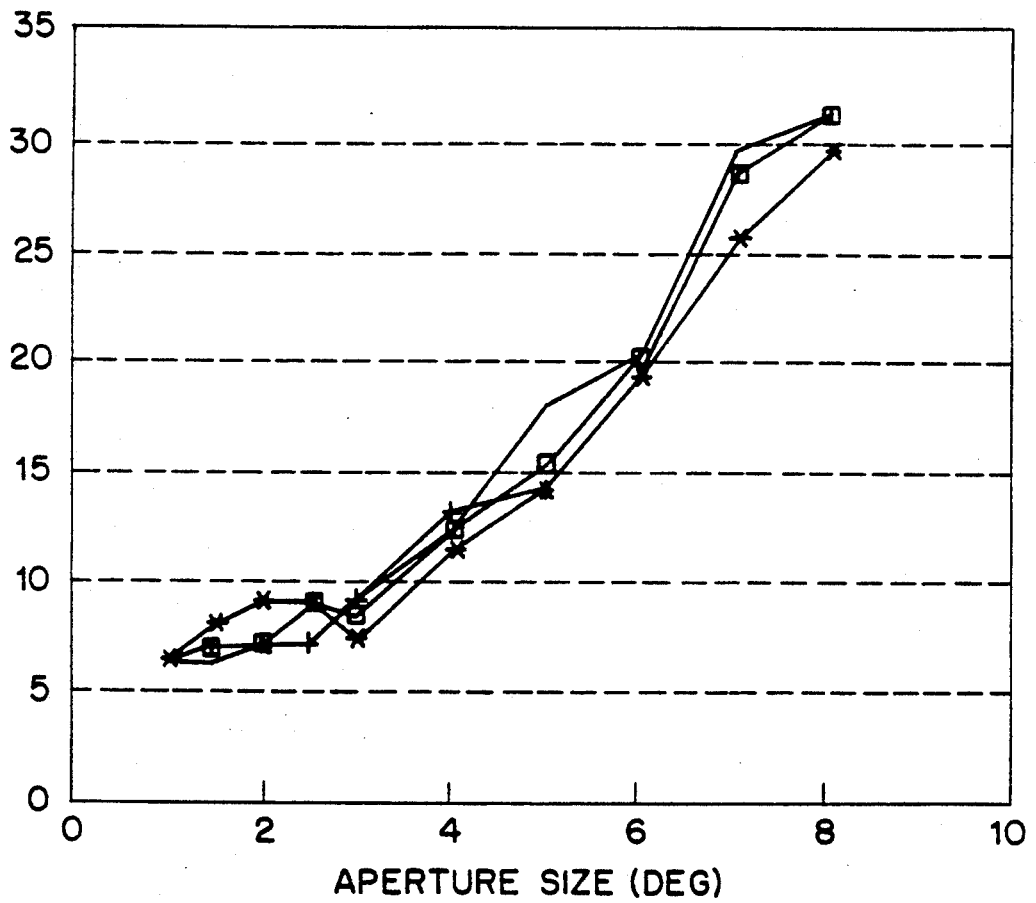
FIG. 4 shows a graph of contrast sensitivity as a function of aperture size for 1 normal individual.
Figure 5:
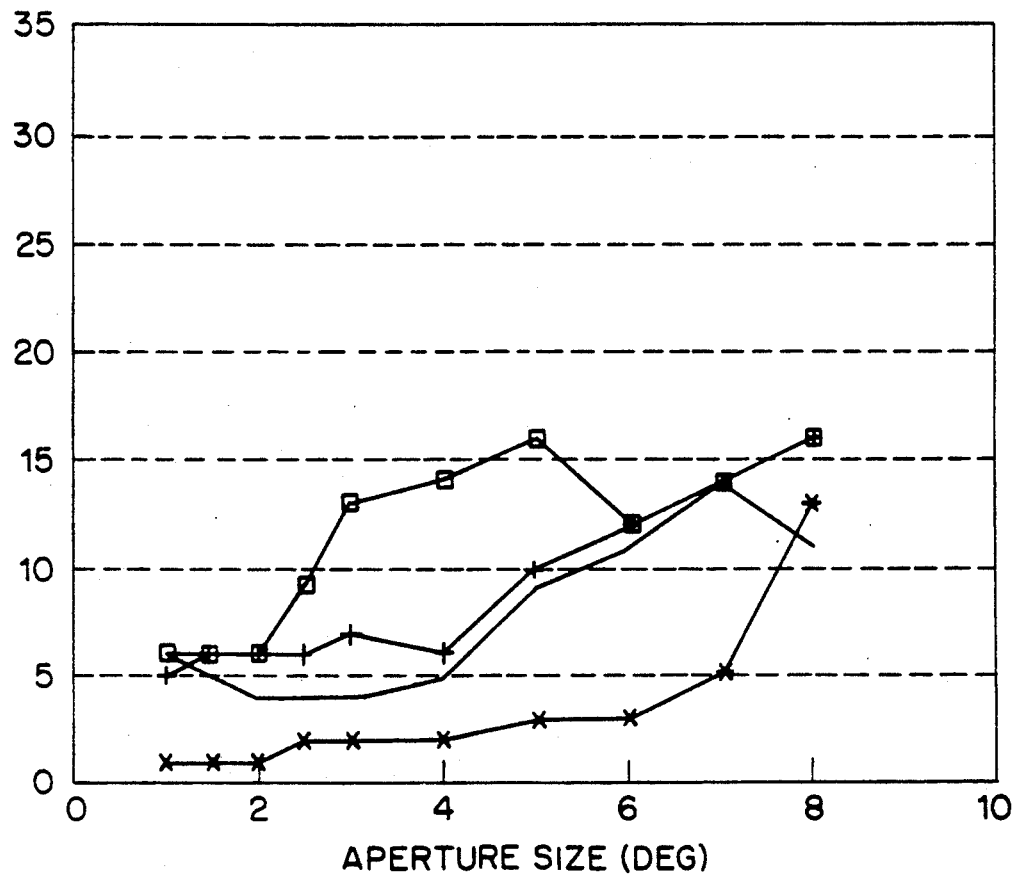
FIG. 5. shows a graph of contrast sensitivity as a function of aperture size for 1 patient with optical neuropathy.
Figure 6:
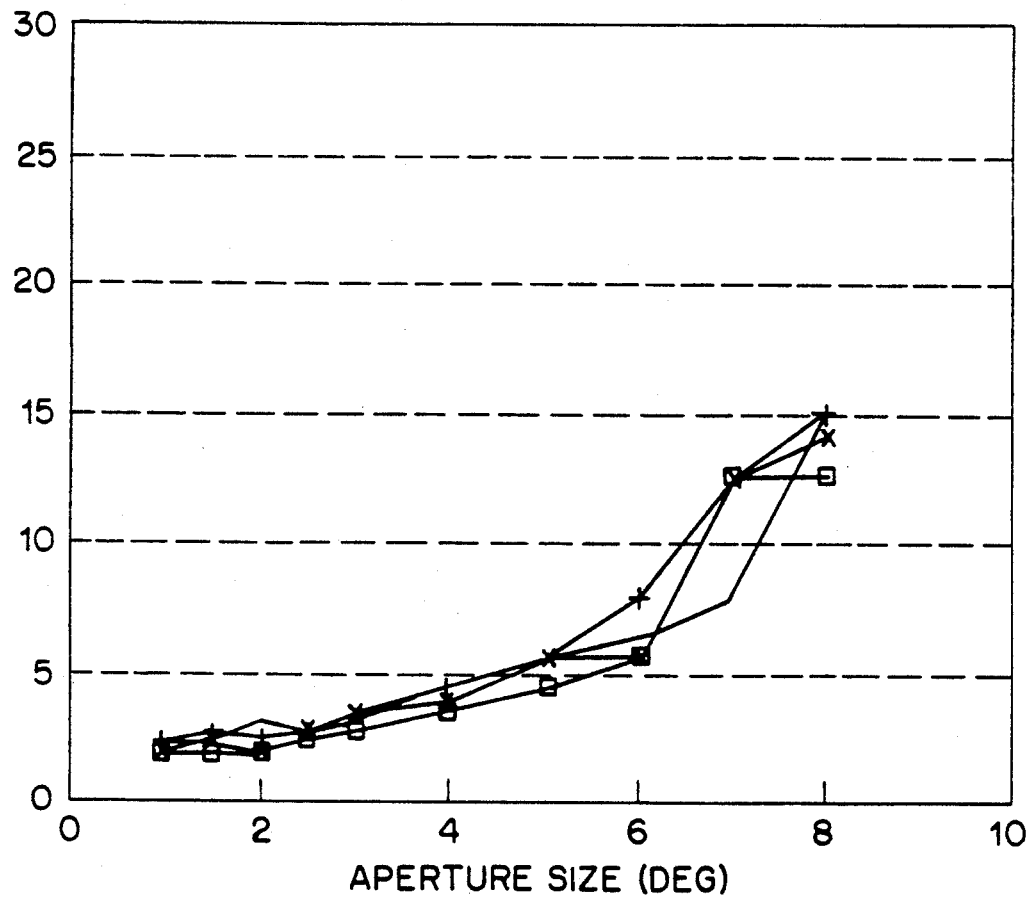
FIG. 6. shows a graph of contrast sensitivity as a function of aperture size for 1 patient with optical neuropathy.

In a further embodiment, the patient is exposed to two or more series of diagnostic images, the series differing in the contrast of the images presented. In this case, monocular contrast sensitivity (CS) for each quadrant can be determined. Contrast sensitivity is defined as the reciprocal of the contrast threshold, where contrast threshold is the lowest level of contrast at which a pattern with a guren spatial frequency and diameter can be detected. Contrast sensitivity also follows a sigmoidal relationship as a function of aperture size in normal patients. (See FIGS. 3 and 4) Observed contrast sensitivity as a function of aperture size in patients diagnosed as having glaucoma, (FIG. 5) and suspected of having glaucoma (FIG. 6) may have a less well defined sigmoidal relationship, but also has a semisaturation constant which is much greater. Again, comparison of the patient value for the semisaturation constant with a standard is diagnostic of the presence or absence of optic neuropathy.

EXAMPLE

Seven normals and 12 patients diagnosed as having various forms of optic neuropathy and cerebral tumors pressing on the optic nerves or optical radiation were presented with individual sinusoidal grating patterns (spatial frequency of 1 c/deg) in each quadrant with the pattern located 4 degrees from fixation. The size of the patterns, measured as the width of the Gaussian aperture at $1/e^4$, ranged from 1 to 8 degrees. The stimuli were presented on an evenly illuminated 14 cm $\times$ 14 cm oscilloscope screen which subtended 10 degrees. Mean luminance was 80 cd/m$^2$.

As shown in FIGS. 3-6, monocular CS as a function of aperture could be described as an S-shaped curve. Abnormal CS function can be grouped as (a) a shift of the function to the right without a slope change or (b) a shift and a slope change. In some patients with apparently intact visual field quadrants, a shift of function without a change in slope was observed.

I claim:

1. Apparatus for detection of optic neuropathy in a patient comprising an optical display system adapted to present to the patient a series of diagnostic images, each of said diagnostic images consisting of a centrally located fixation point and at least four sinusoidal grating patterns truncated by a Gaussian aperture symmetrically disposed about the fixation point, wherein the diameter of the sinusoidal grating patterns varies across the series of diagnostic images.

2. An apparatus according to claim 1, wherein the optical display system is a series of cards, each card having a diagnostic image printed thereon.

3. An apparatus according to claims 2, wherein the diameter of the sinusoidal grating patterns in the diagnostic image subtend from 1 to 16 degrees of visual angle at the intended viewing distance.

4. An apparatus according to claims 2, wherein the diameter of the sinusoidal grating patterns in the diagnostic image subtend from 1 to 8 degrees of visual angle at the intended viewing distance.

5. An apparatus according to claim 2, wherein the optical display system is adapted to present two or more series of diagnostic images to the patient, said series of diagnostic images having different contrast levels.

6. An apparatus according to claim 1, wherein the diameter of the sinusoidal grating patterns in the diagnostic image subtend from 1 to 16 degrees of visual angle at the intended viewing distance.

7. An apparatus according to claim 1, wherein the diameter of the sinusoidal grating patterns in the diagnostic image subtend from 1 to 8 degrees of visual angle at the intended viewing distance.

8. An apparatus according to claim 1, wherein the optical display system is adapted to present two or more series of diagnostic images to the patient, said series of diagnostic images having different contrast levels.

9. A method for detecting of optic neuropathy in a patient comprising
   (a) blocking one eye of the patient to obtain monocular vision;
   (b) presenting to the patient a series of diagnostic images, each of said diagnostic images consisting of a centrally located fixation point and at least four sinusoidal grating patterns truncated by a Gaussian aperture symmetrically disposed about the fixation point, wherein the diameter of the sinusoidal grating patterns varies across the series of diagnostic images;
   (c) comparing the minimum size detected for the patient with a standard value to determine whether optic neuropathy is present.

10. A method according to claim 9, wherein the diagnostic images are presented at a distance such that the diameters of the sinusoidal grating patterns subtend a visual angle of from 1 to 16 degrees.

11. A method according to claim 10, wherein the distance between the fixation point and the centers of the sinusoidal grating patterns subtends a visual angle of about 4 degrees.

12. A method according to claim 10, wherein the diagnostic images are presented at a distance such that the diameters of the sinusoidal grating patterns subtend a visual angle of from 1 to 8 degrees.

13. A method according to claim 9, wherein the diagnostic images are presented at a distance such that the diameters of the sinusoidal grating patterns subtend a visual angle of from 1 to 8 degrees.

14. A method according to claim 9, wherein the diagnostic images are presented on a series of printed cards.

15. A method according to claim 14, wherein the diagnostic images are presented at a distance such that the diameters of the sinusoidal grating patterns subtend a visual angle of from 1 to 16 degrees.

16. A method according to claim 15, wherein the distance between the fixation point and the centers of the sinusoidal grating patterns subtends a visual arc of about 4 degrees.

* * * * *